United States Patent [19]
Stoller et al.

[11] Patent Number: 5,591,730
[45] Date of Patent: Jan. 7, 1997

[54] INHIBITION OF URINARY CALCULI GROWTH

[75] Inventors: Marshall L. Stoller; James S. Wolf, Jr., both of San Francisco, Calif.

[73] Assignee: The Regents of the University of California, Oakland, Calif.

[21] Appl. No.: 134,564

[22] Filed: Oct. 12, 1993

[51] Int. Cl.$^6$ .................................................. A61K 31/66
[52] U.S. Cl. ........................... 514/108; 514/106; 514/891; 424/601; 424/604
[58] Field of Search ...................... 514/108, 106, 514/891; 424/601, 604

[56] References Cited

U.S. PATENT DOCUMENTS

| | | | |
|---|---|---|---|
| 3,683,080 | 8/1972 | Francis | 424/204 |
| 4,134,969 | 1/1979 | Schmidt-Dunker | 424/49 |
| 5,488,041 | 1/1996 | Barbier et al. | 514/108 |

OTHER PUBLICATIONS

Leskovar, P., et al., "A Direct Comparison of the Litholytic Capacity of Renacidin and Some New Calcium Oxalate and/or Phosphate Dissolving Irrigation Systems," *Urolithiasis and Related Clinical Research*, pp. 627–630 (1984).

Curreri, P. A., et al., "A Comparative Appraisal of Adsorption of Citrate on Whewellite Seed Crystals," *J. of Crystal Growth*, 53:209–214 (1981).

Robertson, W. G., et al., "Inhibitors of the Growth and Aggregation of Calcium Oxalate Crystals in vitro," *Clinica Chimica Acta*, 43:31–37 (1973).

Ohata, M., et al., "The effect of diphosphonate on calcium phosphate crystallization in urine in vitro," *Kidney International*, 4:401–406 (1973).

Fraser, D., et al., "The Influence of Disodium Ethane-1-Hydroxy-1,1-Diphosphonate (EHDP) on the Development of Experimentally Induced Urinary Stones in Rats," *Clinical Science*, 42:197–207 (1972).

Fleisch, H., "Bisphosphonates: A New Class of Drugs in Diseases of Bone and Calcium Metabolism," *Recent Results in Cancer Research*, 116:1–28 (1989).

Baumann, J. M., et al., "Biochemical and clinical effects of ethane-1-hydroxy-1,1-diphosphonate in calcium nephrolithiasis," *Clinical Science and Molecular Medicine*, 54:509–516 (1978).

Francis, M. D., et al., "Diphosphonates Inhibit Formation of Calcium Phosphate Crystals in vitro and Pathological Calcification in vivo," *Science*, 165:1264–1266 (19 Sep. 1969).

Barker, M. C. J., et al., "In-vivo labelling of renal calculi with technetium 99m methylene diphosphonate," *British Journal of Radiology*, 55:39–41 (1982).

Corcos, J., et al., "Radio–Contrast Enhancement of Urinary Tract Stones," *J. of Urology*, 145:618–623 (Mar. 1991).

Bone, H. E., III, et al., "Treatment of Calcium Urolithiasis with Diphosphonate Efficacy and Hazards," *J. of Urology*, 121:568–571 (1979).

Pak, C. Y. C., et al., "Effect of diphosphonate on crystallization of calcium oxalate in vitro," *Kidney International*, 7:154–160 (1975).

McCredie, D. A., et al., "Diphosphonate Therapy in Nephrocalcinosis," *British Journal of Urology*, 48:93–100 (1976).

Caniggia, A., et al., "Kinetics of $^{99m}$Technetium–Tin–Methylene–Diphosphonate in Normal Subjects and Pathological Conditions: A Simple Index of Bone Metabolism," *Calcif. Tissue Int.*, 30:5–13 (1980).

*Primary Examiner*—Brian M. Burn
*Attorney, Agent, or Firm*—Townsend and Townsend and Crew LLP

[57] ABSTRACT

The present invention provides metal ion/bisphosphonate complexes that are useful for the treatment and diagnosis of urinary calculi. Preferred bisphosphonates include etidronate, pamidronate (APD), methylene diphosphonate (MDP), and imidodiphosphonate (IDP). The metal ion is preferably a quadrivalent metal ion such as $Sn^{+4}$.

10 Claims, 1 Drawing Sheet

INHIBITION OF URINARY CALCULI GROWTH

BACKGROUND OF THE INVENTION

The present invention relates to compositions and methods for the treatment and diagnosis of urinary calculi. In particular, it relates to the treatment and diagnosis using compositions comprising quadrivalent metal ions and bisphosphonates.

Urinary stones or calculi usually arise because of the breakdown of the balance between the need for kidneys to conserve water and at the same time excrete materials that have low solubility. Although urine contains substances that inhibit crystallization, calcium salts (calcium oxalate or calcium phosphate), uric acid, cystine, and struvite in urine can form crystals which grow and aggregate to form stones. As the stones grow on renal papillae or within the collecting system, they typically do not produce symptoms. The stones may, however, break loose and enter the ureter or occlude the ureteropelvic junction, causing pain and obstruction.

One of the problems facing the physician caring for patients with urinary stone disease is lack of compliance with medical treatment. It is estimated that only 40–60% of patients comply with long-term medical therapies in general. Less frequent dosing intervals are associated with better compliance. Except for twice daily administration for thiazides, medical regimens for calcium urolithiasis usually require 3 to 4 times daily dosing. It can be difficult to convince the average young healthy patient with calcium urolithiasis, who may be asymptomatic between episodes of colic, to remain on one of these medical regimens.

Current medical therapies prevent calcium stone formation by one of two general mechanisms: 1) reduction of the solute concentrations that are the driving physiochemical force for stone formation, either by decreasing the absolute concentration of mineral species (increased fluid intake, cellulose phosphate, orthophosphates, and thiazides) or by complexing active species in the urine (citrate and magnesium); and 2) competition for, or poisoning of, active growth sites on the calculi surface (magnesium, citrate, and orthophosphates). Agents acting through the former mechanism need to be present during any periods of relative supersaturation in order to be effective, which generally requires frequent dosing. Agents inhibiting growth at the calculi surface may or may not need to be present in the urine at all times.

It has been demonstrated that aggregation and growth of both calcium oxalate and calcium phosphate crystals are slowed by bisphosphonates. In particular, etidronate (EHDP), the first bisphosphonate marketed for therapeutic use, was found to reduce calcium oxalate crystalluria in stone-formers (Robertson et al. *Clin. Sci. Mol. Med.* 47:13 (1974)). Subsequent human trials to inhibit calculi formation were disappointing, however, because of incomplete resolution of stone activity and/or excessive musculo-skeletal side-effects. It was thought that since the high doses of EHDP required to constantly inhibit urine crystallization apparently had adverse bone effects, oral EHDP therapy was not promising for urolithiasis. Reports of research efforts with bisphosphonates towards urolithiasis have been rare since 1979.

The prior art thus lacks effective methods of calculi prophylaxis that do not require intensive medical therapy. In particular, inhibitors which bind calculi with great affinity and are not degraded, are particularly desirable because frequent dosing should not be necessary. Such an agent would be very useful clinically, not only for diagnosis and prophylaxis in recurrent stone-formers but also for suppressive therapy in patients with small fragments remaining after lithotripsy. The present invention addresses these and other needs.

SUMMARY OF THE INVENTION

The present invention relates to the use of metal ion/bisphosphonate complexes in the treatment and diagnosis of urinary calculi. The bisphosphonates of the invention have a central P—C—P or P—N—P group variously substituted as described below. Commercially available bisphosphonates such as etidronate, pamidronate (APD), methylene diphosphonate (MDP), and imidodiphosphonate (IDP) can be used. Alternatively, other desired bisphosphonates can be synthesized. The metal ion is preferably a high valence metal ion, typically a quadrivalent metal ion such as $Sn^{+4}$.

Preparation of pharmaceutical compositions comprising the complexes is also disclosed. The pharmaceutical compositions then are used for the treatment and diagnosis of urinary calculi.

DETAILED DESCRIPTION OF THE PREFERRED EMBODIMENTS

Bisphosphonates are analogs of pyrophosphate that bind covalently to mineralized tissue with enormous chemical strength. Fleisch, *Drugs*, 42:919 (1991). The central P—C—P or P—N—P groups, unlike the P—O—P group in pyrophosphate, are resistant to chemical and enzymatic hydrolysis. Many bisphosphonates have been synthesized, with several currently available in the United States for uses including the treatment of osteoporosis (Storm et al. *N. Eng. J. Med.*, 322:1265 (1990)) and Paget's Disease (Harinck et al. *Clin. Orthop. Rel. Res.*, 217:79 (1987)), the amelioration of hypercalcemia of malignancy (Singer et al. *Arch. Int. Med.* 151:471 (1991)), and imaging by nuclear medicine bone scintigraphy (O'mara et al. In: Freeman and Johnson's Clinical Radionuclide Imaging. 3rd ed. Edited by L. M. Freeman. Orlando: Grune and Stratton, pp. 1141, 1984).

The present invention is based in part on the discovery that metal-bisphosphonate complexes have unusually strong affinity for many types of urinary calculi. These complexes are therefore useful for the treatment and diagnosis of urolithiasis. Any of a number of bisphosphonate compounds known to those of skill in the art may be used in the present invention. The preferred bisphosphonates of the invention have the formula:

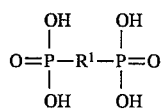

wherein $R^1$ is

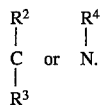

$R^2$ and $R^3$ can be the same or different and are H, hydroxyl, lower alkyl, cycloalkyl, acyl, alkoxy, or aminoalkyl group having the formula:

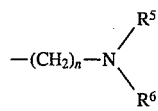

wherein $R^5$ and $R^6$ can be the same or different and are H, lower alkyl, acyl, or alkoxy and n is an integer from 1 to 8.

$R^4$ is H, lower alkyl or aminoalkyl as described above. $R^4$ is preferably H.

As used herein, "alkyl" means a branched or unbranched saturated or unsaturated hydrocarbon group of one to twenty carbon atoms, including lower alkyls having one to eight carbons such as, methyl, ethyl, i-propyl and n-butyl and the like. This definition and the definitions below apply both when the term is used alone and when it is used as part of a compound term, such as "aminoalkyl" and the like.

As used herein, "cycloalkyl" means a cyclic saturated hydrocarbon group of four to seven carbon atoms such as cyclobutyl, cyclopentyl, cyclohexyl and cycloheptyl and the like.

As used herein, "acyl" means an R—CO-group wherein R is an alkyl (typically lower alkyl). Exemplary acyls include $CH_3$—CO— (acetyl).

As used herein, "alkoxy" means an R—O-group wherein R is an alkyl, including lower alkyls. Alkoxies include methoxy, ethoxy and the like.

As used herein, "aminoalkyl" refers to an alkyl group (typically lower alkyl) to which is appended an amine group. The N may be linked to hydrogens or may also be further substituted as in secondary or tertiary amines. A generic formula for such groups is shown above.

Figure 1:
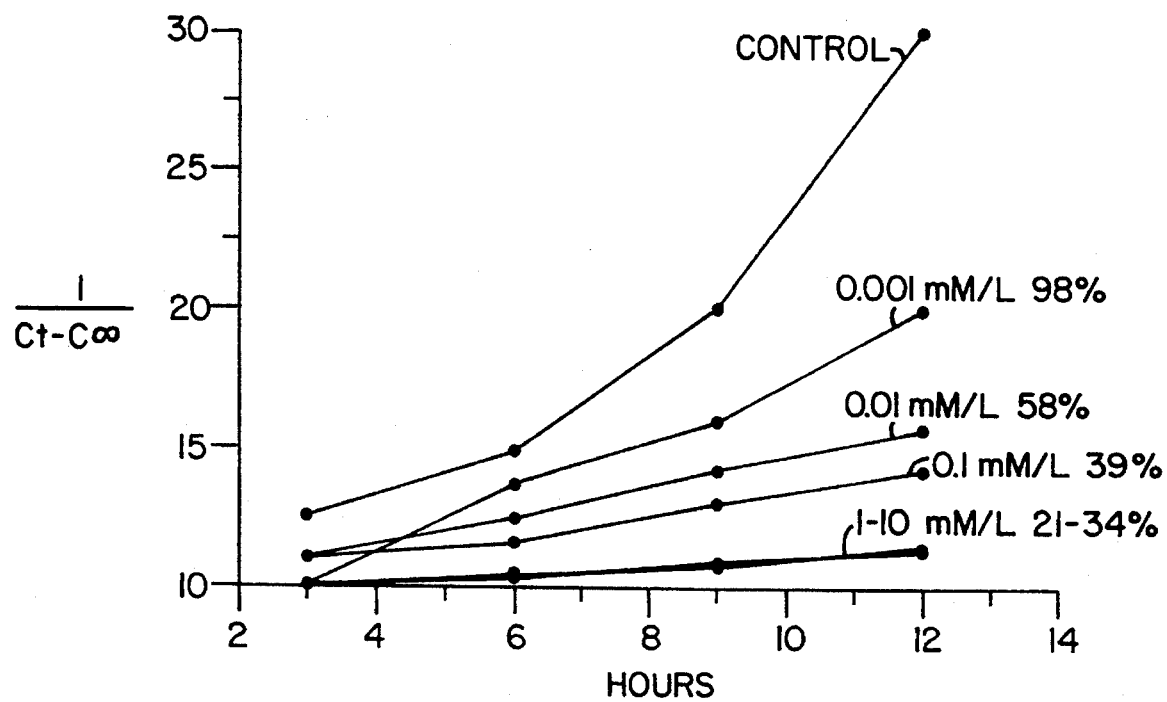
FIG. 1 shows the growth rates associated with seeding with granules that have been incubated with increasing amounts of 1:20 Sn-MDP. The growth rate of the control granules (saline incubation) is included for comparison.
Figure 2A:
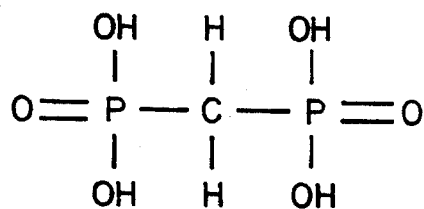
FIG. 2 shows the structures of preferred bisphosphonates of the invention. Methylene diphosphonate, etidronate, and pamidronate are geminal bisphosphonates and are characterized by a central P—C—P group. Imidodiphosphonate, a related compound, has a P—N—P bond instead.
Figure 2B:
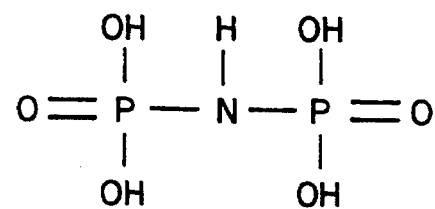
Figure 2C:
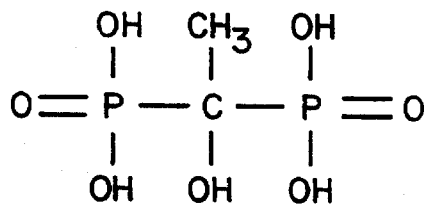
Figure 2D:
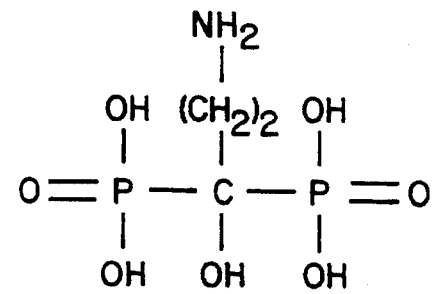

Commercially available bisphosphonates include etidronate, pamidronate (APD), methylene diphosphonate (MDP), and imidodiphosphonate (IDP). Exemplary compounds are illustrated in FIG. 1.

Bisphosphonates suitable for the invention can be synthesized in a variety of ways as described, for instance, in Fleisch *Rec. Results in Cancer Research* 116:1 (1989) and Curry et al., in *Topics in Phosphorous Chemistry* (1972). The commonest method of obtaining 1-hydroxy-1, 1-bisphosphonates is the reaction of the corresponding carboxylic acid with a mixture of $H_3PO_4$ and PCl3. The products obtained under these anhydrous conditions are condensates, i.e., two or more molecules of the bisphosphonate condensed via the removal of a molecule of water. These condensates can then be converted by heating in water or in 6M HCl. Another method consists in using a Michaelis-Arbuzov-like reaction, whereby a carboxylic acid chloride is made to react with a trialkylphosphite. The resultant acylphosphonate reacts under slightly basic conditions with a dialkylphosphite to yield a bisphosphonate tetraalkyl ester, which can then be hydrolyzed with HCl to the corresponding free acid. The 1-amino-1, 1-bisphosphonates are made by reacting a nitrile or an amide with $H_3PO_4$ and a phosphorous trihalide and hydrolyzing the product with water. The reaction can also be carried out directly in the presence of water.

Various methods are available to determine the structure and the purity of bisphosphonates and are used in the synthesis of these compounds. They include, among others, nuclear magnetic resonance techniques (H—NMR, $^{13}$C—NMR, and P—NMR) and gel electrophoresis.

The compositions of the invention comprise the bisphosphonates discussed above complexed to metal ions. The metal ions are typically those that can exist in at least a $^+2$ oxidation state, preferably $^+4$ oxidation state. Any high valence metal ion can be used in the invention. Exemplary metal ions include Sn, Fe, Zn, Pt, Mn, Ru, Rh, Pd and V.

To make the complexes of the invention, a salt of the appropriate metal ion is used, typically chloride salts prepared in hydrochloric acid. The desired bisphosphonate is prepared in the free acid or salt form and the two solutions are added together to produce the desired ratio of metal ion:bisphosphonate. Typically, the ratio is between about 1:1 and 1:10, usually in a range between 1:3 and about 1:6. As explained below, a ratio of 1:4 is preferred.

Pharmaceutical compositions of the invention are suitable for use in both therapeutic protocols and for diagnosis and monitoring of calculi growth. Suitable formulations for use in the present invention are found in *Remington's Pharmaceutical Sciences*, Mack Publishing Company, Philadelphia, Pa., 17th ed. (1985). The pharmaceutical compositions can be used to diagnose or treat a variety of urinary stones, such as calcium, uric acid, cystine, or struvite stones.

The amount administered to the patient will vary depending upon what is being administered, the purpose of the administration, such as prophylaxis or diagnosis, the state of the patient, the manner of administration, and the like. In prophylactic applications, compositions are administered to a patient to prevent further growth of calcium crystals. For instance, the compositions may be administered before, during or after standard therapies (e.g., extracorporeal shockwave lithotripsy, percutaneous ultrasonic lithotripsy) to help prevent regrowth of crystals. An amount adequate to accomplish this is defined as a "prophylactically effective dose." Amounts effective for this use will depend on the severity of the disease and the weight and general state of the patient.

The pharmaceutical compositions are intended for parenteral, oral administration or direct installation into the urinary tract. Commonly, the pharmaceutical compositions are administered parenterally, e.g., intravenously. Thus, the invention provides compositions for parenteral administration which comprise complexes dissolved in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

The concentration of the complexes in the pharmaceutical formulations can vary widely, i.e., from less than about 0.01%, usually at or at least about 5% to as much as 50 to 75% by weight and will be selected primarily by fluid volumes, viscosities, etc., in accordance with the particular mode of administration selected. A typical pharmaceutical composition for intravenous infusion could be made up to contain complexes at a concentration of about $10^{-6}$M to about $10^{-1}$M for therapeutic uses. For diagnostic applications, the concentrations will typically be between about 10 and about 50 mM.

For intravenous administration, the concentration of the complexes will vary according to, for example, the particular use for which the treatment is made, the manner of administration of the complexes, the health and condition of the patient, and the judgment of the prescribing physician. Because the complexes bind urinary stones with high affinity, the dosing intervals can be extended. For example, for the treatment of urinary calculi, the dosing interval can be daily, or 1 to 4 times per month using a dose of about 20 cc to the unilateral collecting system.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more complexes of the invention, preferably 25–75%.

Labeled complexes of the present invention can be used in a variety of in vitro or in vivo applications. For in vitro applications, the assay formats described below are particularly useful. For any of these purposes, the complexes may be directly or indirectly labeled. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, etc. Those of ordinary skill in the art will know of other suitable labels for binding to the complexes, or will be able to ascertain such using routine experimentation. The binding of these labels is achieved using standard techniques common to those of ordinary skill in the art.

For in vivo diagnostic imaging of urinary stones gamma-emitting radioisotopes, typically technetium-99, are typically used in accordance with well known techniques. The radioisotopes are typically bound to the complex directly. The complexes can also be labeled with a paramagnetic isotope for use in magnetic resonance imaging (MRI) or electron spin resonance (ESR), both of which were well known.

In general, any conventional method for visualizing diagnostic imaging can be used. Usually gamma- and positron-emitting radioisotopes are used for camera imaging and paramagnetic isotopes are used for MRI. Thus, the complexes can be used to detect urinary stones or monitor for the presence of stones after standard therapies. By detecting small stones using these methods, the clinician can determine whether a particular therapeutic regimen aimed at eliminating the stones is effective.

The following examples illustrate, but do not limit, the invention.

EXAMPLE 1

This example describes an in vitro assay useful for testing metal ion/bisphosphonate complexes of the invention. The assay detects growth of calcium crystals by measuring a decrease in calcium ion activity in solution.

MATERIALS AND METHODS

All solutions were made up in distilled and de-ionized water (dd $H_2O$) to an ionic strength of 0.15 with sodium and chloride as the supporting electrolytes. Solution pH was brought within the range of 6–7 with the addition of sodium hydroxide or hydrochloric acid. Commercially obtained chemicals without further purification were used: methylene diphosphonic acid (MDP) (Fluka Chemika-Biochemika, Switzerland); citric acid, hydrochloric acid, and stannous chloride, (Sigma Chemical Company, St. Louis, Mo.); sodium hydroxide (Aldrich Chemical Company, St. Louis, Mo.); calcium chloride and sodium oxalate (Fisher Scientific, Pittsburgh, Pa.); and sodium chloride (Mallinkrodt Incorporated, Paris, Ky.).

Incubation

Composition of renal calculi obtained from 6 patients following open or percutaneous nephrolithotomy was determined by a commercial laboratory (Calculab, Hoffman-LaRoche Laboratories, Richmond, Va.). The calculi were ground with a mortar and pestle to fine granules and were sifted through a pair of wire mesh sieves (Bel-art Products, Pequannock, N.J.). Granules that passed through a sieve with 90 µm openings and were retained by a sieve with 63 µm openings were rinsed extensively with dd $H_2O$ to remove adherent particles. The resulting granules, between 63 µm and 90 µm in diameter, were dried in air and stored in a sealed container. Uniformity of the granules was confirmed with light microscopy (Nikon 111682 microscope, Japan).

Into 15 cc polystyrene centrifuge tubes (Corning Incorporated, Corning, N.Y.) were placed 5 mg of the calculi granules and 5 cc of an incubating solution as described on page 15, lines 23–36, below. The granules were incubated at 25° C. for several hours on a rotating mixer (Scientific Equipment Products, Baltimore, Md.). The granules were then centrifuged at 20 gravities for 15 seconds (Dynac centrifuge, Becton Dickinson and Company, Parsippany, N.J.) and the supernatant was evacuated. The granules were washed 3 times with 10 cc saline, each time centrifuging the granules down and removing the supernatant to leave a volume <0.1 cc.

Crystal Growth Assay

Stock solutions of 0.60 mM/L calcium chloride and 0.60 mM/L sodium oxalate were made up weekly and stored in glass containers. Ten cc of each stock solution were added dropwise into flat bottomed polyurethane cups (Sarstedt, W. Germany) that had been rinsed 3 times with dd $H_2O$. Into each cup, now containing 20 cc of a supersaturated solution of calcium and oxalate (0.30 mM/L each), was added 5 mg of the incubated and washed calculi granules to "seed" the solution and initiate crystal growth. The cups were gently agitated at 25° C. on a rotary shaker (Janke and Kunkel, W. Germany) with an excursion of 4 mm at a rate of 100 excursions per minute.

Calcium Electrode

A liquid-membrane calcium ion-selective electrode (Orion Research Incorporated, Boston, Mass.), in conjunction with a silver/silver chloride reference electrode (Orion), measured the activity of ionic calcium in solution as the indicator of crystal growth. When interfering ions are kept constant the device has a lower limit of detection to <0.01 mM/L calcium, with reproducibility of ±4%, according to the manufacturer. Voltage potentials were translated into molarity readings by the pH/ion meter (Accumet 25 pH meter, Fisher Scientific) after calibration with calcium oxalate standards made from the same stock as the crystal growth assay solutions. Readings were obtained at set intervals following initiation of crystal growth. The system was recalibrated before every set of readings to correct for alterations in the response of the electrode. Restandardization was performed during readings as needed to correct for minor drift that occurred without alteration of the response curve.

Calculation of Growth Rates

The method of Meyer and Smith was used to calculate growth rates (Meyer and Smith *Invest. Urol.* 13:31 (1975)). Growth of calcium oxalate crystals in a supersaturated system is a second order phenomenon that can be represented by the integrated equation:

$$1/(C_t-C\infty)=kt+A$$

where $C\infty$ is the calcium concentration in mM/L at equilibrium, $C_t$ is the calcium concentration in mM/L at time t in hours, k is the growth rate in $(mM \text{ hour}/L)^{-1}$ and A is a constant of integration. A decrease in $C_t$ indicates deposition of calcium oxalate on the calculi surface. $C_t$ and $C\infty$ are measured by the calcium electrode. As $C_t$ approaches $C\infty$ the growth rate is no longer adequately represented by the second order equation. Data from the first 75% of the growth period were therefore used to calculate k. Unless otherwise indicated, the growth rates reported are relative to the rate of crystal growth after seeding with 5 mg of granules that had been incubated in saline (control):

$$\text{Relative rate} = k_{test\ solution} / k_{control}$$

Runs were generally performed in duplicate. The mean relative rate is reported.

RESULTS

Growth Rates of Saline-Incubated Granules

Calculi from several individuals were used to make seed granules. Microscopy confirmed that the granules were uniform with little contamination by smaller particles. Composition and relative growth rates after seeding with 5 mg of the saline-incubated granules are listed in Table 1. Among the 4 types of granules with at least 80% calcium oxalate (types I–IV, Table 1) there was variation in growth rates but the calcium activity in all seeded growth assays consistently proceeded towards an equilibrium value of 0.20 mM/L. The pH of the solutions remained between 6 and 7. In contrast, 2 types of granules with 40% or greater composition of calcium phosphate demonstrated an initial loss of calcium from solution followed by a rise in calcium activity. Growth rates could not be calculated with the second order equation. The pH of the solution increased when the calcium activity increased, suggesting that some of the calcium phosphate dissolved.

Altering the amount of the granules used to seed the crystal growth assay produced an approximately linear proportional change in growth rates. The growth curves associated with seeding with 2 mg, 5 mg, 10 mg, and 20 mg of type II granules were determined. The growth rates (relative to 5 mg of type II granules) were 0.46, 1.0, 2.04, and 3.42 respectively.

Observation of the crystal growth assay system revealed that there was some precipitation of calcium oxalate from the supersaturated solution even in the absence of seed granules. When a 0.30 mM/L solution of calcium and oxalate was left in the polyurethane cup without the addition of granules the relative "growth rate" (representing the rate of precipitation of calcium) was 3%. Thus there was some loss of calcium from solution attributable to the system alone, but this appeared to be minimal relative to the rate following seeding.

Growth Rates of Inhibitor-Incubated Granules

After incubation with several potential inhibitors of stone growth, the resulting growth rates revealed which agents inhibited growth via activity at the calculi surface. Several inhibitors and their associated relative growth rates are listed in Table 2. Citrate had no effect on stone growth in this assay, whereas MDP complexed to stannous ion (Sn) had a potent inhibitory effect. In contrast, both agents inhibited growth when added directly to the supersaturated calcium oxalate solution in the crystal growth assay (data not shown).

When Sn-MDP was added to 5 mg of types I, II, III, and IV granules, the growth rates (relative to the saline-incubated granules of each respective type) were 0.25, 0.26, 0.38, and 0.23 respectively. Thus, while there was variation in the growth rate associated with the different saline-incubated granules, the relative inhibition of growth by Sn-MDP was similar for all granules. Sn-MDP incubation with varying amounts of type II granules had a different result. In this case, the growth rates (relative to the same amount of saline-incubated Type II granules) were 0.66, 0.26, 0.20, and 0.07 for 2 mg, 5 mg, 10 mg, and 20 mg of granules respectively. The absolute growth rates, however, were similar to each other at 0.57, 0.38, 0.78, and 0.43 $(Mm\ \text{hour}/L)^{-1}$, respectively.

In conclusion, the pre-adsorbed calculi growth assay evaluates the effect of potential growth inhibitors at the surface of granules derived from real human calculi. Limiting the inhibitory effect to the stone surface provides insight into the mechanism of inhibition. Additionally, the new model includes the matrix component in the seed material in an effort to more closely approximate physiologic nucleation sites. These findings indicate that citrate is an inhibitor of calcium oxalate crystal growth by way of activity in solution but not via interactions at the stone surface. The Sn-MDP complex is active both in solution and at the stone surface.

TABLE 1

Relative Growth Rates Associated with 5 mg of Saline-Incubated Granules

| Granule Type | Composition | Growth Rate (relative to type I) |
|---|---|---|
| I | 80% calcium oxalate 20% calcium phosphate | 1.00 |
| II | 85% calcium oxalate 15% calcium phosphate | 2.59 |
| III | 90% calcium oxalate 10% calcium phosphate | 1.05 |
| IV | 80% calcium oxalate 10% calcium phosphate 10% uric acid | 0.53 |

TABLE 2

Inhibition of Growth Associated with 5 mg of Type I Granules

| Inhibitor | Concentration of Inhibitor | Growth Rate (relative to saline-incubation) |
| --- | --- | --- |
| Citrate | 100 mM/L | 0.97 |
| Sn-Citrate* | 1 mM/L | 1.00 |
| MDP | 100 mM/L | 0.97 |
| Sn-MDP* | 1 mM/L | 0.24 |

*1:10 molar ratio of Sn to citrate or MDP.

EXAMPLE 2

This example demonstrates the ability of the complexes of the invention to inhibit growth of urinary calculi as demonstrated using the assays described above.

MATERIALS AND METHODS

Chemicals were purchased commercially: methylene diphosphonic acid (MDP) (Fluka Chemika-Biochemika, Switzerland); citric acid, hydrochloric acid, imidodiphosphonate sodium, magnesium chloride, platinic chloride, sodium hydrosulfite, stannous chloride, and zinc chloride (Sigma Chemical Company, St. Louis, Mo.); sodium hydroxide (Aldrich Chemical Company, St. Louis, Mo.); calcium chloride and sodium oxalate (Fisher Scientific, Pittsburgh, Pa.); ferric chloride and sodium chloride (Mallinkrodt Incorporated, Paris, Ky.); and etidronate disodium (MGI Pharma, Minneapolis, Minn.). Pamidronate disodium was generously provided by Ciba Pharmaceutical Company, Summit, N.J. Reagents were used as received without further purification. All solutions were made in distilled and de-ionized water (dd $H_2O$) at a pH of 6-7 and with an approximate ionic strength of 0.15 using sodium and chloride as supporting electrolytes.

Solutions of metal ion:ligand complexes were prepared in a uniform fashion. The chloride salt of the metal was used in all cases: Zinc[II] ($Zn^{2+}$), Iron[III] ($Fe^{3+}$), Magnesium[II] ($Mg^{2+}$), Platinum[IV] ($Pt^{4+}$), and Tin[II] ($Sn^{2+}$). Each was dissolved in concentrated hydrochloric acid (HCl), which was fumed on a hot plate for 2 minutes to ensure dissolution of the metal salt. The ligands were prepared in their acid form (MDP, citrate) or in their salt form (IDP, EHDP, APD). A sufficient amount of the metal-HCl solution was added to solutions of the ligands to produce complexes with various metal:ligand molar ratios (1:1, 1:10, etc.). The pH was brought to 6-7 with the addition of sodium hydroxide. Solutions containing sodium hydrosulfite or solutions of metal ions alone were made up in dd $H_2O$ without an HCl intermediate.

Preparation and incubation of seed granules, the crystal growth assay, and growth rate calculation were performed as described above. In a variation of the crystal growth assay designed to assess the longevity of the inhibitory effect of the test solutions, the granules were placed into 50 cc polyurethane cups following the incubation step. Saline containing 3 mM/L calcium chloride was dripped into the cups at a rate of 500 cc/day. After 1, 2, or 7 days the granules were recovered from the cups, washed 3 times in the same manner as the other granules, and used to seed the crystal growth assay.

RESULTS

Metal Ion Complexes with Citrate and MDP

Solutions of metal ions complexed with citrate and MDP were made up in the ratios noted in Table 3. All solutions were clear, without evidence of precipitation, except for the 1:1 complexes of Mg-MDP, Fe-citrate, Zn-MDP, and Sn-citrate. Relative growth rates after incubation with metal ion:ligand complexes are tabulated in Table 3. Table 4 lists the results after incubation with the uncomplexed metal ions or ligands individually. Neither citrate nor MDP alone had any effect on growth rate up to a concentration of 100 mM/L. The only metal ion to inhibit growth when used alone was Fe, which at a concentration of 1 mM/L slowed growth to 64% of control. This compares to the inhibition of growth by Fe-citrate and Fe-MDP, also at 1 mM/L (in a 1:1 ratio), to 76% and 74% of control, respectively. Complexes with Mg or Zn had no effect. The 1:1 complex of Pt-MDP held growth to 63% of control. Since $SnCl_2$ is insoluble in $H_2O$ at pH 6-7, Sn alone could not be tested. In complex with citrate, however, Sn had minimal inhibitory effect only at the 1:1 ratio (81% of control). The strongest effect in this series of incubating solutions was by Sn-MDP solutions, which inhibited calculi growth to 23-50% of control at ratios from 1:1 to 1:100.

The reducing agent sodium hydrosulfite was also tested. Whether alone at a concentration of 1 mM/L or complexed with citrate or MDP in a ratio of 1:10 (1 mM/L ligand), sodium hydrosulfite had no effect in the crystal growth assay.

The inhibitory effect of Sn-MDP varied with the ratio of Sn to MDP. Ratios of 1:4 and 1:10 were the most potent. In addition, growth inhibition by Sn-MDP was concentration dependent, as illustrated in FIG. 2.

Other Bisphosphonates

In addition to MDP, 3 other phosphonates were tested: imidodiphosphonate sodium (IDP), etidronate disodium (EHDP), and pamidronate disodium (APD). The latter two compounds are bisphosphonates like MDP, but IDP is a different analog of pyrophosphate (see FIG. 1). It is characterized by a central P—N—P group rather than a P—C—P group as in the bisphosphonates. MDP, IDP, and EHDP behaved similarly in that they did not inhibit calculi growth without the addition of Sn (Table 5). When complexed to Sn (1:20 ratio, 2 mM/L ligand), these 3 compounds inhibited growth to 24-25% of control. APD had more potent inhibitory effects by a factor of 3, both alone (31% of control) and in a complex with Sn (9% of control).

Longevity of Inhibition

Investigators evaluating the longevity of bisphosphonate inhibition of calcification on porcine heart valves found that calcium was necessary to keep the bisphosphonates adsorbed to the surface (Johnston et al., *J. Pharm. Sci.* 77:740 (1988). The present studies confirmed this, showing that the inhibitory effect of adsorbed Sn-MDP was lost after 24 hours of rinsing with 150 mM/L NaCl with 3 mM/L calcium chloride. This solution was used to rinse the incubated granules for 1-7 days. A 10 mM/L solution of 1:10 Sn-MDP, which caused inhibition of calculi growth to 21% of control in the pre-adsorbed crystal growth assay, inhibited growth to 44%, 19%, and 45% of control after 1, 2, and 7 days of rinsing, respectively.

Conclusion

The potentiation of bisphosphonate activity by Sn was considerable. The mechanism of Sn potentiation of bisphosphonates in the crystal growth assay is probably not related to the reducing capacity of $Sn^{2+} \rightarrow Sn^{4+}$ because the other reducing agent evaluated, sodium hydrosulfite, had no effect in combination with MDP. Additionally, the oxidation of Sn in room air occurs within just a few days. The Sn-MDP solutions, although closed during storage, were certainly exposed to enough air to allow oxidation of the Sn ion. The activity of the agent nonetheless did not change over the course of months.

Without wishing to be bound by theory, it seems more likely that Sn was effective in its $^{+4}$ oxidation state. Each of the phosphonate groups of a bisphosphonate molecule are thought to act as separate unidentate ligand, such that one group could bind the $Sn^{+4}$ ion and the other would be free to bind onto the growth sites of the calcium oxalate crystal. If, in the $^{+4}$ oxidation state, one Sn ion can bind 4 bisphosphonate molecules, the entire complex would have 4 phosphonate groups exposed to the exterior. That 4 bisphosphonate molecules bind to the Sn ion is suggested by the finding that a 1:4 ratio of Sn to MDP was 1 of the 2 most potent of the Sn:MDP complexes.

There may be additional effects of the Sn ion in conjunction with bisphosphonates. Some investigators have reported that Sn slightly inhibits calcium oxalate growth, while others deny there is an effect. Sn alone could not be tested at the 1 mM/L concentration in our assay because of insolubility, but in combination with citrate there was a slight growth inhibitory effect. Sn therefore may add some inherent inhibitory potential to the bisphosphonate complex. Fe also appears to inhibit calcium oxalate crystal growth by itself; this persists without change in the presence of MDP or citrate. Other investigators also have found Fe:citrate to inhibit calcium oxalate growth.

In conclusion, the complex of metal ions with bisphosphonates had strong inhibitory effects in a calcium oxalate crystal growth assay that measured activity at the calculi surface. Sn was the most potent metal ion and APD was the most potent bisphosphonate; together they slowed the growth of calculi granules to 9% of control. This prominent effect compares to the minimal effect of other metal ions (Mg, Fe, Zn, and Pt) and citrate. The inhibition by Sn-bisphosphonate complexes persisted despite a week of continual rinsing, thus raising the possibility that only infrequent dosing may be required. Such regimens might be considered for prophylaxis of calcium oxalate calculi but they are probably best suited for the prevention of regrowth of small residual fragments following lithotripsy.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

TABLE 3

Growth Inhibition by Metal:Citrate or Metal:MDP Complexes
(1 mM/L of Ligand)
Metal:Ligand Ratio

|  | 1:1 | 1:10 | 1:100 |
|---|---|---|---|
| Mg-Citrate | 1.04* | 1.02 | 1.00 |
| Mg-MDP | 1.02 | 1.00 | 1.02 |
| Fe-Citrate | 0.76 | 0.90 | 1.03 |
| Fe-MDP | 0.74 | 0.91 | 1.00 |
| Zn-Citrate | 0.89 | 0.85 | 1.03 |
| Zn-MDP | 0.91 | 1.06 | 1.05 |

TABLE 3-continued

Growth Inhibition by Metal:Citrate or Metal:MDP Complexes
(1 mM/L of Ligand)
Metal:Ligand Ratio

|  | 1:1 | 1:10 | 1:100 |
|---|---|---|---|
| Pt-Citrate | 1.06 | 1.22 | 1.24 |
| Pt-MDP | 0.63 | 0.86 | 0.98 |
| Sn-Citrate | 0.81 | 1.00 | 1.04 |
| SN-MDP | 0.50 | 0.23 | 0.31 |

*Growth rate relative to calculi incubated with saline.

TABLE 4

Growth Inhibition by Metal Ions or Ligands Alone
Concentration

|  | 100 mM/L | 10 mM/L | mM/L |
|---|---|---|---|
| Mg | — | — | 0.98* |
| Fe | — | — | 0.64 |
| Zn | — | — | 0.90 |
| Pt | — | — | 0.98 |
| Sn | — | — | — |
| Citrate | 0.97 | 1.05 | — |
| MPD | 0.97 | 0.90 | — |

*Growth rate relative to calculi incubated with saline.

TABLE 5

Growth Inhibition by Other Phosphonates

|  | Phosphonate | | | |
|---|---|---|---|---|
|  | MDP | IDP | EHDP | ADP |
| Alone (10 mM/L) | 0.90* | 0.97 | 0.93 | 0.31 |
| 1:20 ratio with Sn (2 mM/L Ligand) | 0.24 | 0.25 | 0.24 | 0.09 |

*Growth rate relative to calculi incubated with saline.

What is claimed is:

1. A method of inhibiting the growth of urinary tract calculi in a patient, the method comprising administering to the patient a prophylactically effective amount of a pharmaceutical composition comprising a pharmaceutically acceptable carrier and a metal ion-bisphosphonate complex, wherein the metal can exist in at least a $^{+2}$ oxidation state.

2. The method of claim 1, wherein the bisphosphonate has the formula:

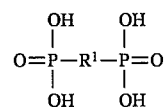

wherein $R^1$ is

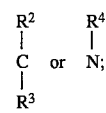

and wherein $R^2$ and $R^3$ are the same or different and are selected from the group consisting of H, hydroxyl, lower alkyl, acyl, cycloalkyl, alkoxy and the group:

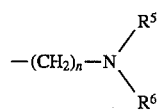

wherein $R^5$ and $R^6$ can be the same or different and are selected from the group consisting of H, lower alkyl, acyl, and alkoxy; n is an integer from 1 to 8; and $R^4$ is selected from the group consisting of H, lower alkyl and aminoalkyl.

3. The method of claim 2, wherein $R^1$ is

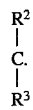

4. The method of claim 3, wherein $R^2$ and $R^3$ are H.

5. The method of claim 3, wherein $R^2$ is methyl and $R^3$ is hydroxyl.

6. The method of claim 3, wherein $R^2$ is aminoethyl and $R^3$ is hydroxyl.

7. The method of claim 1, wherein the metal ion is in a $^{+4}$ oxidation state.

8. The method of claim 7, wherein the metal ion is $Sn^{4+}$.

9. The method of claim 1, wherein the pharmaceutical composition is administered by direct installation.

10. The method of claim 1, wherein the pharmaceutical composition is administered after lithotripsy.

* * * * *